United States Patent
Simha et al.

(10) Patent No.: US 11,670,419 B2
(45) Date of Patent: Jun. 6, 2023

(54) SELECTED PRE-HOSPITAL TREATMENT BASED ON WIRELESS NETWORK COMMUNICATION IN A FIFTH GENERATION (5G) OR OTHER NEXT GENERATION NETWORK

(71) Applicant: AT&T Mobility II LLC, Atlanta, GA (US)

(72) Inventors: Prathima Simha, Great Falls, VA (US); Benjamin Bell, Dallas, TX (US); Craig Leonardi, San Ramon, CA (US); Robert Sloan, Westfield, NJ (US); Scott Agnew, Crofton, MD (US); Scott Mendoza, Dallas, TX (US); Mingwun Li, Dallas, TX (US)

(73) Assignee: AT&T Mobility II LLC, Atlanta, GA (US)

( * ) Notice: Subject to any disclaimer, the term of this patent is extended or adjusted under 35 U.S.C. 154(b) by 83 days.

(21) Appl. No.: 16/911,676

(22) Filed: Jun. 25, 2020

(65) Prior Publication Data

US 2021/0407665 A1 Dec. 30, 2021

(51) Int. Cl.
*G16H 40/67* (2018.01)
*G16H 50/70* (2018.01)
(Continued)

(52) U.S. Cl.
CPC .......... *G16H 40/67* (2018.01); *A61B 5/7282* (2013.01); *G16H 40/63* (2018.01); *G16H 50/20* (2018.01); *G16H 50/70* (2018.01)

(58) Field of Classification Search
CPC ........ G16H 40/67; G16H 40/20; G16H 80/00; G16H 50/70
See application file for complete search history.

(56) References Cited

U.S. PATENT DOCUMENTS

2009/0054029 A1\* 2/2009 Hogberg ............ H04L 41/5006
455/404.2
2014/0286160 A1\* 9/2014 Zhang ................ H04L 47/2433
370/230
(Continued)

FOREIGN PATENT DOCUMENTS

WO WO-2011127459 A1 \* 10/2011 ............. G16H 10/60

OTHER PUBLICATIONS

Hosseini, Mohammad, Richard B. Berlin, and Lui Sha. "Physiology-aware rural ambulance routing." 2017 IEEE International Conference on Healthcare Informatics (ICHI). IEEE, 2017. (Year: 2017).\*

*Primary Examiner* — Linh Giang Le
*Assistant Examiner* — Constantine Siozopoulos
(74) *Attorney, Agent, or Firm* — Amin, Turocy & Watson, LLP

(57) ABSTRACT

The technologies described herein are generally directed to facilitating operation of a health network control system. In accordance with one or more embodiments, systems described herein can include a processor, and a memory that can store executable instructions that, when executed by the processor, can facilitate performance of operations that can include facilitating receiving, from transceiver of a second device, a first signal that can describe an event related to treatment of the treatment subject. Further, the operations can include, based on an analysis of the subject information, the event information and facility information representative of a group of treatment facilities, selecting a treatment facility that can perform the treatment of the treatment subject, resulting in a selected treatment facility, and facilitating communicating via a second signal to the transceiver of the second device, selected facility information corresponding to the selected treatment facility.

20 Claims, 10 Drawing Sheets

(51) Int. Cl.
*G16H 40/63* (2018.01)
*A61B 5/00* (2006.01)
*G16H 50/20* (2018.01)

(56) References Cited

U.S. PATENT DOCUMENTS

2017/0235898 A1* 8/2017 Coulter .......... G06Q 10/063114
 705/2
2018/0314798 A1* 11/2018 Hernandez ............. G16H 50/20

* cited by examiner

SELECTED PRE-HOSPITAL TREATMENT BASED ON WIRELESS NETWORK COMMUNICATION IN A FIFTH GENERATION (5G) OR OTHER NEXT GENERATION NETWORK

TECHNICAL FIELD

The subject application is related to the use of networked information in a 5G or other next generation wireless communication system, and, for example, providing treatment information by a wireless network.

BACKGROUND

Treatment by first responders and other pre-hospital providers has become more important as the demand for healthcare generally increases. Additionally, the variety and usefulness of services that can be provided onsite has increased significantly because of improvements in networking and processing technologies. For example, for pre-hospital services, fifth generation (5G) wireless communications can provide increased bandwidth, reduced latency, improved reliability, and improvements in the accuracy of geolocation by mobile devices.

Even with the improvements in networking technology, first responders can encounter problems administering treatments, e.g., treating patients at accident/health emergency scenes. For example, just providing increased bandwidth cannot integrate onsite information about the condition of a patient with isolated information stored in different systems. In addition, although provider networks can have the capacity to prioritize certain types of important communications, often this prioritizing can be misapplied to lower importance communications or not applied to communications of higher importance.

BRIEF DESCRIPTION OF THE DRAWINGS

The technology described herein is illustrated by way of example and not limited in the accompanying figures in which like reference numerals indicate similar elements and in which.

DETAILED DESCRIPTION

Figure 1:
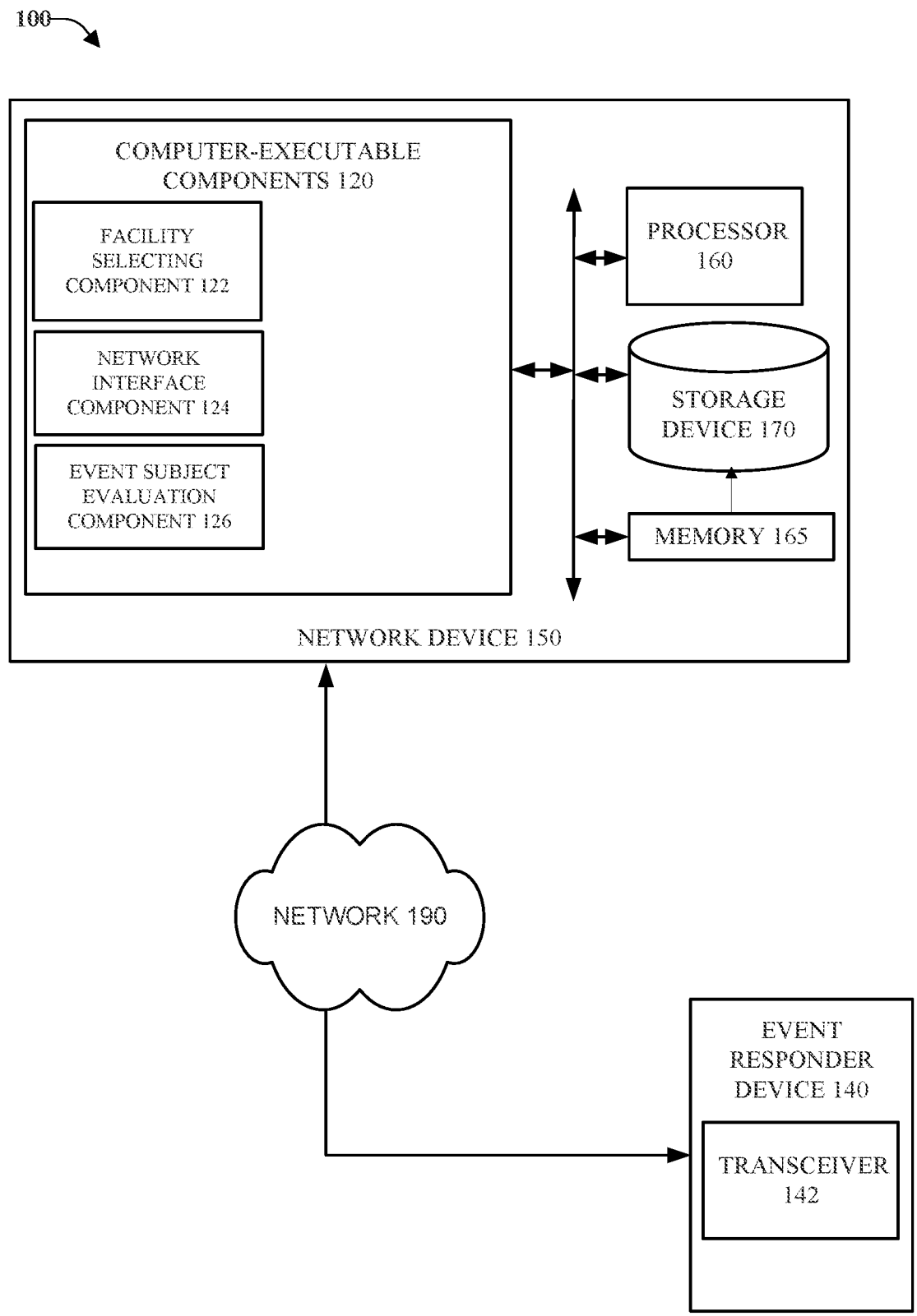
FIG. 1 is an architecture diagram of an example system that can facilitate operation of a health network control system of information sharing, in accordance with one or more embodiments.

Generally speaking, one or more embodiments described herein can facilitate operation of a health network control system of information sharing, using different approaches. In addition, one or more embodiments described herein can be directed towards a multi-connectivity framework that supports the operation of New Radio (NR, sometimes referred to as 5G). As will be understood, one or more embodiments can allow an integration of user devices with network assistance, by supporting control and mobility functionality on cellular links (e.g. long term evolution (LTE) or NR). One or more embodiments can provide benefits including, system robustness, reduced overhead, and global resource management, while facilitating direct communication links via a NR sidelink.

It should be understood that any of the examples and terms used herein are non-limiting. For instance, while examples are generally directed to non-standalone operation where the NR backhaul links are operating on mmWave bands and the control plane links are operating on sub-6 GHz LTE bands, it should be understood that it is straightforward to extend the technology described herein to scenarios in which the sub-6 GHz anchor carrier providing control plane functionality could also be based on NR. As such, any of the examples herein are non-limiting examples, any of the embodiments, aspects, concepts, structures, functionalities or examples described herein are non-limiting, and the technology may be used in various ways that provide benefits and advantages in radio communications in general.

In some embodiments the non-limiting term "radio network node" or simply "network node," "radio network device," "network device," and access elements are used herein. These terms may be used interchangeably, and refer to any type of network node that can serve user equipment and/or be connected to other network node or network element or any radio node from where user equipment can receive a signal. Examples of radio network node include, but are not limited to, base stations (BS), multi-standard radio (MSR) nodes such as MSR BS, gNodeB, eNode B, network controllers, radio network controllers (RNC), base station controllers (BSC), relay, donor node controlling relay, base transceiver stations (BTS), access points (AP), transmission points, transmission nodes, remote radio units (RRU) (also termed radio units herein), remote ratio heads (RRH), and nodes in distributed antenna system (DAS).

In some embodiments the non-limiting term user equipment (UE) is used. This term can refer to any type of wireless device that can communicate with a radio network node in a cellular or mobile communication system. Examples of UEs include, but are not limited to, a target device, device to device (D2D) user equipment, machine type user equipment, user equipment capable of machine to machine (M2M) communication, PDAs, tablets, mobile terminals, smart phones, laptop embedded equipped (LEE), laptop mounted equipment (LME), USB dongles, and other equipment that can have similar connectivity. In one or more embodiments, D2D can be used to transfer data between medical devices measuring patient vitals and the responder mobile device. Similarly, M2M (Machine to machine) communication—this may be used by the responder's device or hospital system to directly receive patient vitals from a medical device measuring a patient's vitals, e.g., EKG data or a scanned image Example UEs are described further with FIGS. 9 and 10 below. Some embodiments are described in particular for 5G new radio systems. The embodiments are however applicable to any radio access technology (RAT) or multi-RAT system where the UEs operate using multiple carriers, e.g. LTE.

The computer processing systems, computer-implemented methods, apparatus and/or computer program products described herein employ hardware and/or software to solve problems that are highly technical in nature (e.g., decoding wireless signals to determine patient information, rapidly analyzing different treatment options, and allocating network resources based on patient status), that are not abstract and cannot be performed as a set of mental acts by a human. For example, a human, or even a plurality of humans, cannot efficiently integrate wireless data receipt and demodulation (which generally cannot be performed manually by a human) and detailed analysis of treatment options, with the same level of accuracy and/or efficiency as the various embodiments described herein.

Aspects of the subject disclosure will now be described more fully hereinafter with reference to the accompanying drawings in which example components, graphs and operations are shown. In the following description, for purposes of explanation, numerous specific details are set forth in order to provide a thorough understanding of the various embodiments. However, the subject disclosure may be embodied in many different forms and should not be construed as limited to the examples set forth herein.

Generally speaking, in one or more embodiments, a network device can facilitate a health network control system that can enable different functions such as the integration of relevant information across otherwise unconnected systems, network resource allocation based on a status of a patient, selection of treatment facilities based on factors including network connectivity, analysis of historical data to support current resource selection, and incorporation of sensors and information of a patient's mobile device into onsite treatment decisions and selection of treatment facilities.

FIG. 1 is an architecture diagram of an example system 100 that can facilitate operation of a health network control system of information sharing, in accordance with one or more embodiments. For purposes of brevity, description of like elements and/or processes employed in other embodiments is omitted.

System 100 can include network device 150 communicatively coupled to event responder device 140 via network 190. According to multiple embodiments, network device 150 can include memory 165 that can store one or more computer and/or machine readable, writable, and/or executable components 120 and/or instructions that, when executed by processor 160, can facilitate performance of operations defined by the executable component(s) and/or instruction(s).

In some embodiments, memory 165 can comprise volatile memory (e.g., random access memory (RAM), static RAM (SRAM), dynamic RAM (DRAM), etc.) and/or non-volatile memory (e.g., read only memory (ROM), programmable ROM (PROM), electrically programmable ROM (EPROM), electrically erasable programmable ROM (EEPROM), etc.) that can employ one or more memory architectures. Further examples of memory 165 are described below with reference to system memory 1006 and FIG. 10. Such examples of memory 165 can be employed to implement any embodiments of the subject disclosure.

According to multiple embodiments, processor 160 can comprise one or more processors and/or electronic circuitry that can implement one or more computer and/or machine readable, writable, and/or executable components and/or instructions that can be stored on memory 165. For example, processor 160 can perform various operations that can be specified by such computer and/or machine readable, writable, and/or executable components and/or instructions including, but not limited to, logic, control, input/output (I/O), arithmetic, and/or the like. In some embodiments, processor 160 can comprise one or more components including, but not limited to, a central processing unit, a multi-core processor, a microprocessor, dual microprocessors, a microcontroller, a System on a Chip (SOC), an array processor, a vector processor, and other types of processors. Further examples of processor 160 are described below with reference to processing unit 1004 of FIG. 10. Such examples of processor 160 can be employed to implement any embodiments of the subject disclosure.

In exemplary embodiments, event responder device 140 can be used by first responders dispatched to a geographic location where a person is in need of treatment. In this example, event responder device 140 can exchange data via network 190 with network device 150. Additional details, alternative, and additional embodiments are discussed with FIGS. 2-5 below.

Figure 2:
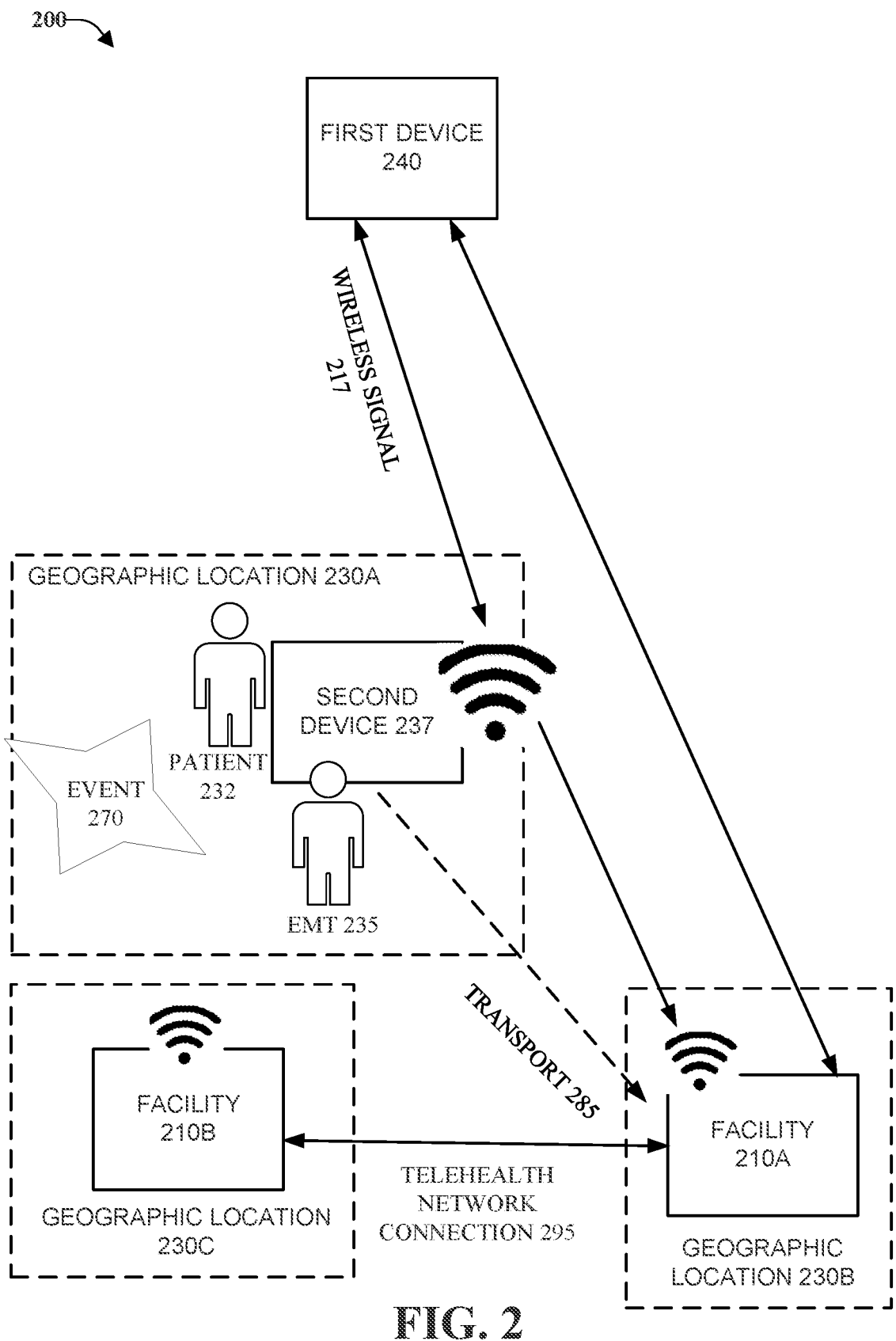
FIG. 2 illustrates an example diagram of physical and communication links between multiple geographic locations in a health network control center, in accordance with one or more embodiments.

FIG. 2 illustrates an example diagram 200 of physical and communication links between multiple geographic locations 230A-C in a health network control center, in accordance with one or more embodiments. For purposes of brevity, description of like elements and/or processes employed in other embodiments is omitted. Diagram 200 includes first device 240 and geographic locations 230A-C. Facilities 210A-B are located at geographic locations 230B-C respectively. Event 270 occurs with respect to patient 232 at geographic location 230A, and emergency medical technician 235 responds with second device 237.

Different terms can be used herein to broadly describe many aspects of example embodiments. For example, as discussed with exemplary embodiments above, event responder device 140 (e.g., second device 230) can be used by first responders (e.g., emergency medical technicians (EMT) 235 and other emergency medical services (EMS) entities) dispatched to a geographic location (e.g., geographical location 210A being the location of event 270) where a person is in need of treatment, e.g., because of event 270. Notwithstanding the above-provided example, and other examples provided herein being directed to patients 232, EMT 235 responders, and other medical entities, these examples are non-limiting, and the spirit of one or more embodiments described herein can also be applied to other, non-medical contexts. For example, in one or more additional embodiments, device 140 can be one used by a hospital to transfer one of its patients to another facility, e.g., device 140 can be used by a hospital worker to look for the health care facility that is best transfer facility depending on factors including, but not limited to, a patient's condition, facility/services needed, and what facilities are available close by.

Returning to the computer-executable components 120 of FIG. 1, in an example discussed with FIG. 2, memory 165 can store computer and/or machine readable, writable, and/or executable components 120 and/or instructions that, when executed by processor 160, can facilitate execution of the various functions described herein relating to network device 150, e.g., facility selecting component 122, network interface component 124, and event subject evaluation component 126, as well as other components to implement and provide functions to system 100 and some other embodiments described herein.

It should be appreciated that the embodiments of the subject disclosure depicted in various figures disclosed herein are for illustration only, and as such, the architecture of such embodiments are not limited to the systems, devices, and/or components depicted therein. For example, in some embodiments, network device 150 can further comprise various computer and/or computing-based elements described herein with reference to operating environment 1000 and FIG. 10. In one or more embodiments, such computer and/or computing-based elements can be used in connection with implementing one or more of the systems, devices, components, and/or computer-implemented operations shown and described in connection with FIG. 1 or other figures disclosed herein.

In one or more embodiments, memory 165 can store executable instructions that, when executed by processor 160, facilitate generation of a network interface component, which can in some implementations facilitate receiving, from a transceiver of a second device, a first wireless signal that is modulated to encode subject information representative of a treatment subject and event information describing an event related to the treatment subject occurring at a geographic location proximate to the second device, wherein the event implicates a treatment of the treatment subject. For example, in one or more embodiments, network interface component 124 can facilitate receiving, from a transceiver 142 of a second device 237, a first wireless signal 217 that is modulated to encode subject information representative of a treatment subject (e.g., patient 232) and event information describing an event 270 related to the treatment subject occurring at a geographic location 230A proximate to the second device 237, wherein the event 270 implicates a treatment of the treatment subject, e.g., emergency medical treatment of patient 232.

In one or more embodiments, memory 165 can further store executable instructions that, when executed by processor 160, facilitate generation of a facility selecting component, which can, in some implementations, based on an analysis of the subject information and the facility information representative of a group of treatment facilities, select a treatment facility of the group of treatment facilities to perform the treatment of the treatment subject, resulting in a selected treatment facility. For example, in one or more embodiments, facility selecting component 122 can, based on an analysis of the subject information and facility information representative of a group of treatment facilities 210A-B, select a treatment facility 210A of the group of treatment facilities to perform the treatment of the treatment subject (e.g., patient 232), resulting in a selected treatment facility 210A.

In one or more embodiments, memory 165 can further store executable instructions that, when executed by processor 160, facilitate generation of an event subject evaluation component, which can in some implementations, based on an further analysis of information that includes the subject information and the event information, select a treatment facility of the group of treatment facilities to perform the treatment of the treatment subject, resulting in a selected treatment facility. For example, in one or more embodiments, event subject evaluation component 126 can, based on further analysis of information that includes the subject information and the event 270 information, select a treatment facility 210A of the group of treatment facilities to perform the treatment of the treatment subject, resulting in a selected treatment facility.

In one or more embodiments, the network interface component can further facilitate communicating via a second wireless signal to the transceiver of the second device, selected facility information corresponding to the selected treatment facility. For example, in one or more embodiment, network interface component 124 can facilitate communicating via a second wireless signal 217 to the transceiver 142 of the second device 237, selected facility information corresponding to the selected treatment facility 210A.

Returning to the healthcare example provided above, in one or more embodiments, event 270 can reference an event that has caused patient 232 to be in need of treatment, e.g., a heart attack, a car accident, or a fall. Event 270 can be the cause of the dispatch of first responders, e.g., EMT 235. One or more embodiments can incorporate information about event 270 (e.g., event information) with other information (e.g., patient information), to generate selections of different treatment options, e.g., to which of facilities 210A-B should patient 232 be transported 285. For example, information about what type of event occurred (e.g., a traumatic event, cardiac, or neurological) can be used to allocate priority to network resources allocated (e.g., discussed further below) as well as which of facilities 210A-B is selected for transport 285, e.g., facility 210A can be a trauma center, with the treatment capabilities of the facility used to evaluate the assignment of patient 232 thereto. Treatment facilities 210A-B can be broadly interpreted to include transport destinations for EMT 235, e.g., a hospital emergency room, an urgent care, and physician's office.

An additional treatment facility available for selection by one or more embodiments is a telehealth facility, e.g., facility 210B coupled to facility 210A by telehealth network connection 295. One having skill in the relevant art(s), given the description herein, would appreciate the telehealth network connection 295 can facility caregivers at facility 210A to provide treatment remotely by resources at telehealth facility 210B. In one or more embodiments, telehealth capabilities can facilitate treatment by hospital with advanced care physicians/facilities using technologies including, but not limited to, advanced video capabilities, remote robotic devices, augmented reality, and virtual reality capabilities.

With respect to telehealth treatments, in addition to the treatment resources that can be provided with the pair of facilities 210A-B, one or more embodiments can evaluate the relative capabilities of telehealth network connection 295, e.g., bandwidth, latency, and reliability. This evaluation can be incorporated into facility selection in different ways, including whether the connection can support the types of treatment implicated by the status of patient 232, e.g., remote surgery, video consults, distribution of high-definition imagery, and can require different network capacities.

Another way that the performance status of telehealth network connection 295 can be used by one or more embodiments, is the active adjustment of network resources based on the availability of treatment throughout the system, the treatments implicated for patient 232, and the current status of patient 232. For example, if facility 210B is evaluated to be a possible transport destination (e.g., proximity to geographic location 230A, treatments available by telehealth connection with facility 210A, and the urgency of treatment of patient 232), one or more embodiments can evaluate the strength of telehealth network connection 295 to determine whether changes can be made to improve the quality of the link, e.g., so as to facilitate the availability telehealth facility 210B as a transport destination for treatment.

It should be appreciated that, in some embodiment, the functions of the health network control center (e.g., network device 150) can be managed by a wide area network provider and, as such in some implementations, network resources can be beneficially reallocated based on different considerations. In a general example, second device 237 utilized by EMT 235 can have an initial preferential priority allocated based on a status as a healthcare responder. Beyond this undifferentiated, broad allocation of resources based on status, one or more embodiments can further allocate preferential priority based on the severity of event 270, the status of patient 232, the amount of other patients 232 in the area who require treatment, the technologies estimated to be required for treatment, and other similar considerations.

One approach to allocating priority to responder devices is by allocating network slices to one or more communications processes. In one or more embodiments, network slices can be described as virtual networks with independent sets of logical network functions that can be selected to support particular requirements of different network applications. Applications, as a part of execution, can request allocation of a network slice having certain characteristics to facilitate successful program execution. Example characteristics of network slices can include, but are not limited to, location, speed, connectivity, latency, security, energy use, coverage, and capacity. Example, network slices configured with certain characteristics for certain applications, are discussed below.

For example, even before EMT 235 arrives at geographic location 230A, the severity of event 270 can be estimated, e.g., by voice recognition of oral reports and by electronic dispatching data for EMT 235. Based on this estimated severity, an initial priority level can be assigned to the response to event 270 by EMT 235. In addition, once on scene, a status of patient 232 can be determined (e.g., by monitoring measuring devices such as blood pressure and by entry of EMT 235), and the priority assigned to communications supporting the treatment of patient 235 can be adjusted, if needed. Later, during transport, a change in status of patient 232 can further cause one or more embodiments to adjust network priority for treatment of patient 232.

In additional example implementations, additional network characteristics can be adjusted by one or more embodiments. For example, if warranted by analysis of conditions, one or more embodiments can elevate network links associated with treatment of patient 232 to a higher quality of service (QoS), e.g., by setting a higher QoS class identifier (QCI) and allocation and retention priority (ARP) values for the relevant links. In some circumstances, this approach can increase the efficiency of network resource allocation by considering resource allocations to an incident-level of granularity.

Returning to a discussion of allocating network slices to different aspects of embodiments, in the example above, several example elements can be addressed by network slices designed and allocated to event responder device 140 and network device 150 to handle different tasks described and suggested by descriptions herein. For example, video interactions between network device 150 and responder device 140 are described herein, and to maintain allocations of network resources, one or more embodiments can allocate a network slice with characteristics including, but not limited to, increased speed, lower latency, and increased security, with all of these resources being useful in some circumstances for supporting video treatment options. One having skill in the relevant art(s), given the description herein would appreciate that, to keep track of, and control these allocated resources, service level agreements (SLAs) can be used by one or more embodiments.

Figure 3:
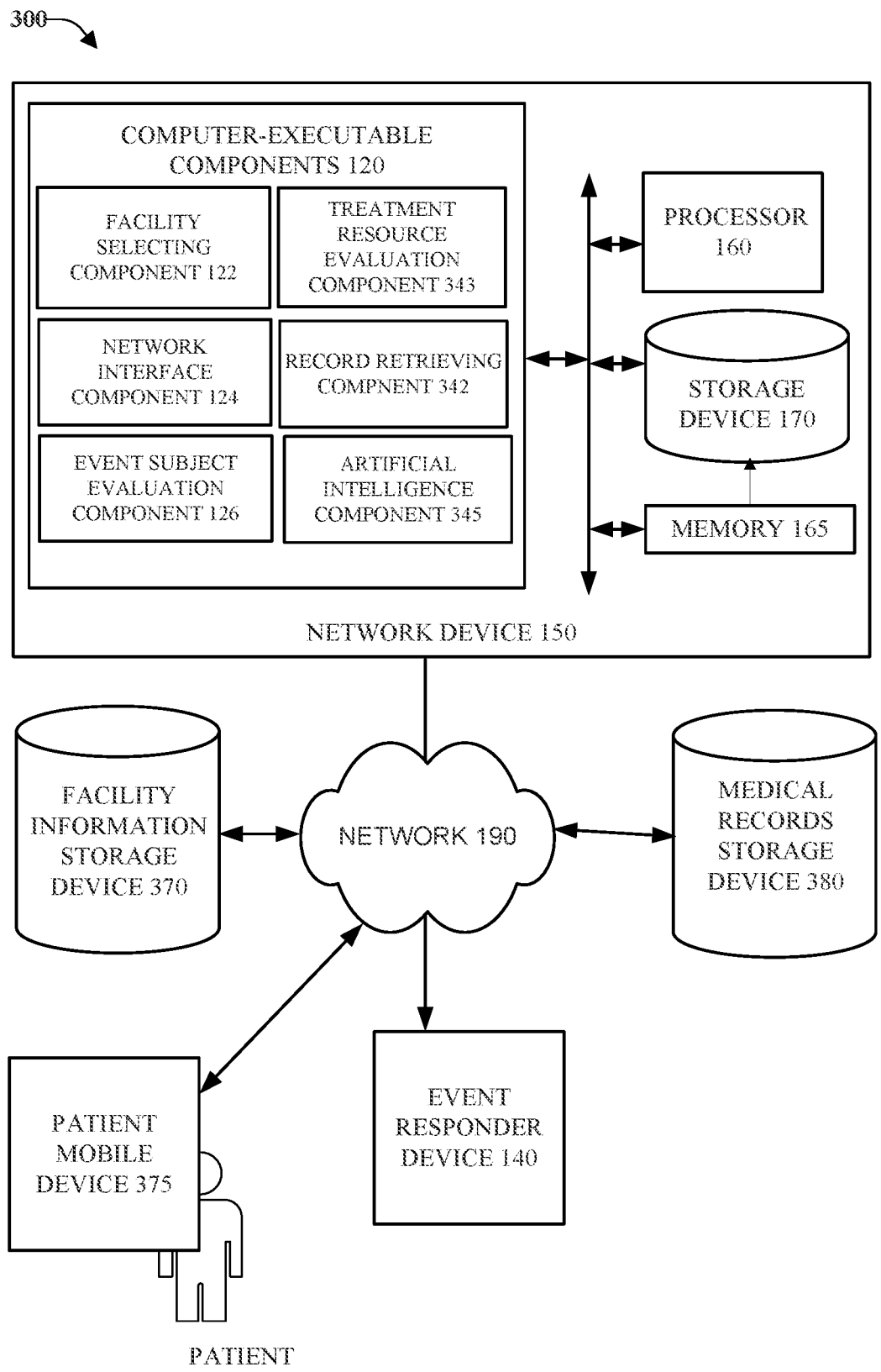
FIG. 3 is an architecture diagram of an example system that can facilitate selecting from different treatment facilities for a subject where treatment is implicated, in accordance with one or more embodiments.

FIG. 3 is an architecture diagram of an example system 300 that can facilitate selecting from different treatment facilities for a subject where treatment is implicated, in accordance with one or more embodiments. For purposes of brevity, description of like elements and/or processes employed in other embodiments is omitted. System 100 can include network device 150 communicatively coupled via network 190 to event responder device 140, facility information storage device 370, medical records storage device 380, and patient mobile device 375 with patient 232.

According to multiple embodiments, network device 150 can include memory 165 that can store one or more computer and/or machine readable, writable, and/or executable components 120 and/or instructions that, when executed by processor 160, can facilitate performance of operations defined by the executable component(s) and/or instruction (s).

In an example, memory 165 can store computer and/or machine readable, writable, and/or executable components 120 and/or instructions that, when executed by processor 160, can facilitate execution of the various functions described herein relating to network device 150, e.g., facility selecting component 122, network interface component 124, and event subject evaluation component 126, treatment resource evaluation component 343, record retrieving component 342, artificial intelligence component 345, as well as other components to implement and provide functions to system 300 and some other embodiments described herein. In one or more embodiments, the analysis of different factors can include the use of artificial intelligence component 345 in different ways, with different approaches and examples being discussed with FIG. 6 below.

In one or more embodiments, event responder device 140 (e.g., also termed second device in FIG. 2) can facilitate pre-hospital assessment and treatment of patients 232. For example, by integrating pre-hospital treatment information about patient 232 from medical devices that provide vitals and diagnostics, external information, one or more embodiments can facilitate a more accurate assessment of the status of patient 232, e.g., including information retrieved from medical records storage device 275. In addition, one or more embodiments can facilitate selection of a treatment facility 210A-B (e.g., by facility selecting component 122) based on information retrieved from facility information storage device 370, discussed further below with FIG. 4 and a discussion of treatment resources.

Additionally, in FIG. 3, patient 232 is depicted with patient mobile device 375. It should be appreciated that one or more embodiments can, when permitted, access information relevant to treatment choices directly from patient mobile device 375. For example, patient mobile device can contain information regarding past medical history, pre-existing conditions, living-will preferences, hospital preferences, insurance provider and coverage, and other similar, information that can be potentially useful to functions of one or more embodiments.

Continuing the healthcare example from above, mobile device 375 can have automatedly sensed the occurrence of event 270 (e.g., a cardiac event from an onboard monitory, an automobile accident from accelerometer and gyroscope), and have contacted health services to provide identifying information and request a response to event 270 at geographic location 230A. Based on the identifying information, one or more embodiments can retrieve medical records, etc. Alternatively, if records are not available based on an identification of patient 232 by patient mobile device 375, one or more embodiments (e.g., of network device 150) can query patient mobile device for information previously permitted to be shared in this context.

Figure 4:
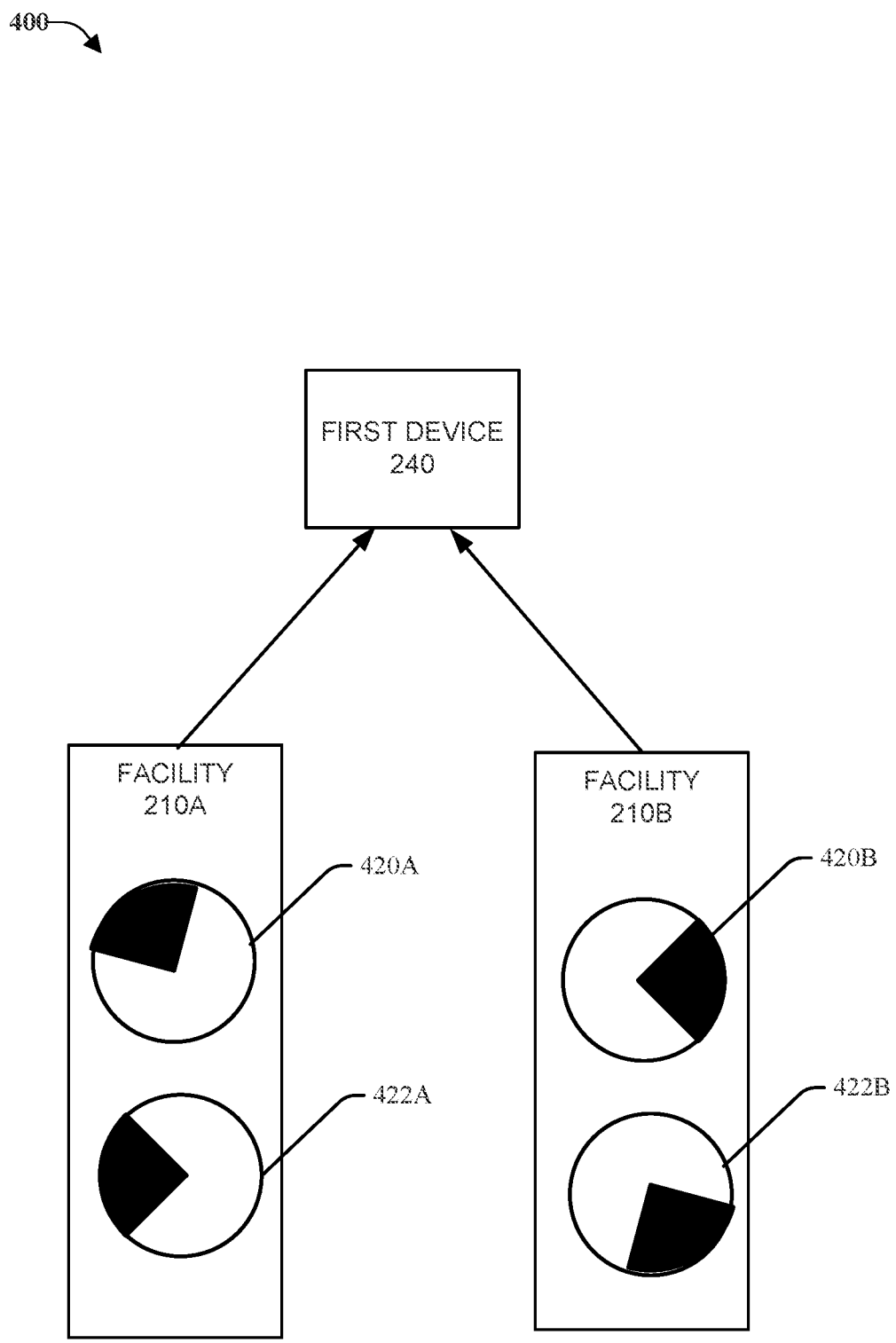
FIG. 4 includes diagram illustrating treatment resource availabilities of facilities linked to first device 240, in accordance with one or more embodiments.

FIG. 4 includes diagram 400 illustrating treatment resource availabilities of facilities linked to first device 240, in accordance with one or more embodiments. For purposes of brevity, description of like elements and/or processes employed in other embodiments is omitted. Diagram 400 includes first device 240 communicatively linked to facilities 210A-B. Facilities 210A-B include indications of treatment resource availabilities 420A-B and 422A-B, respectively.

As noted above, one or more embodiments can evaluate different criteria and select from different treatment options for patient 232, e.g., from available treatment facilities 210A-B. As further noted above, different determinations by one or more embodiments can be based on evaluation of current conditions, e.g., a changing patient 232 status. Similarly, as illustrated with FIG. 4, treatment resource availabilities 420A-B or 422A-B can be determined (e.g., by first device 240) to be potentially significant for treatment of patient 232, and as such, current assessments the availability of these resources can be utilized when selecting from facilities 210A-B and, if these assessments change, updated determination can be made.

Figure 5:
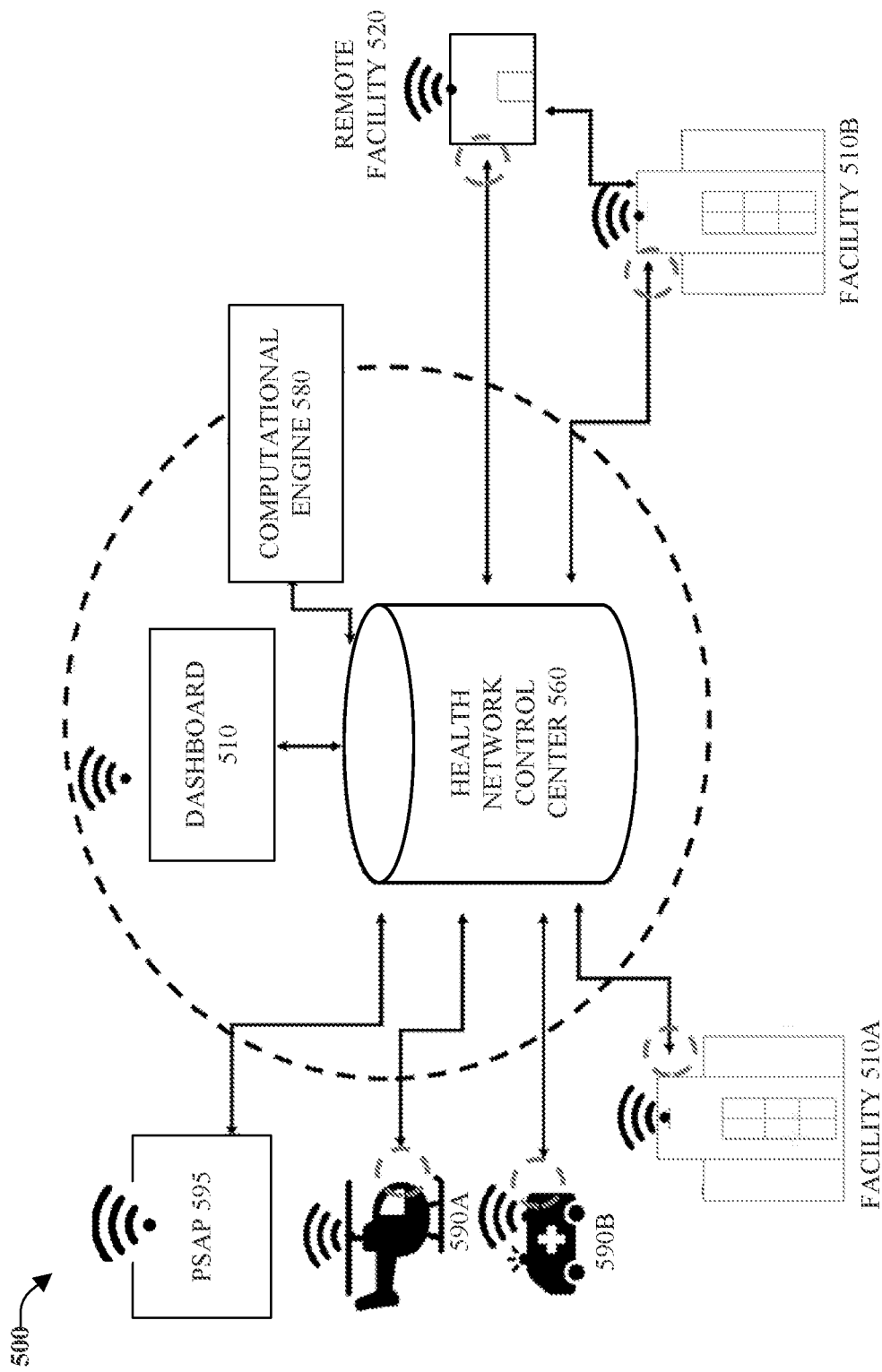
FIG. 5 depicts an example implementation of health network control system with health network control center linked to multiple data sources, treatment resources, and responsive resources, in accordance with one or more embodiments.

FIG. 5 depicts an example implementation of health network control system 500 with health network control center 560 linked to multiple data sources, treatment resources, and responsive resources, in accordance with one or more embodiments. For purposes of brevity, description of like elements and/or processes employed in other embodiments is omitted. Health network control system 500 includes health network control center 560, responder vehicles 590A-B, facilities 510A-B, and remote facility 520. Health network control center 560 is communicatively coupled to computational engine 580, and dashboard 525.

As depicted in FIG. 5, one or more embodiments can capture information form public safety access points (PSAP) (e.g., 911-call centers) to initially collect information about event 270, geographical location 210A, and patient 232. As noted above with FIGS. 2-3, one or more embodiments can initially assign network resources to responders, based on a potential need for higher-performance connections. Collecting information from PSAPs 595 can provide information that can be integrated with other information sources, e.g. medical records of patient 232 and information on patient mobile device 375 that is permitted to be shared in this context.

Figure 6:
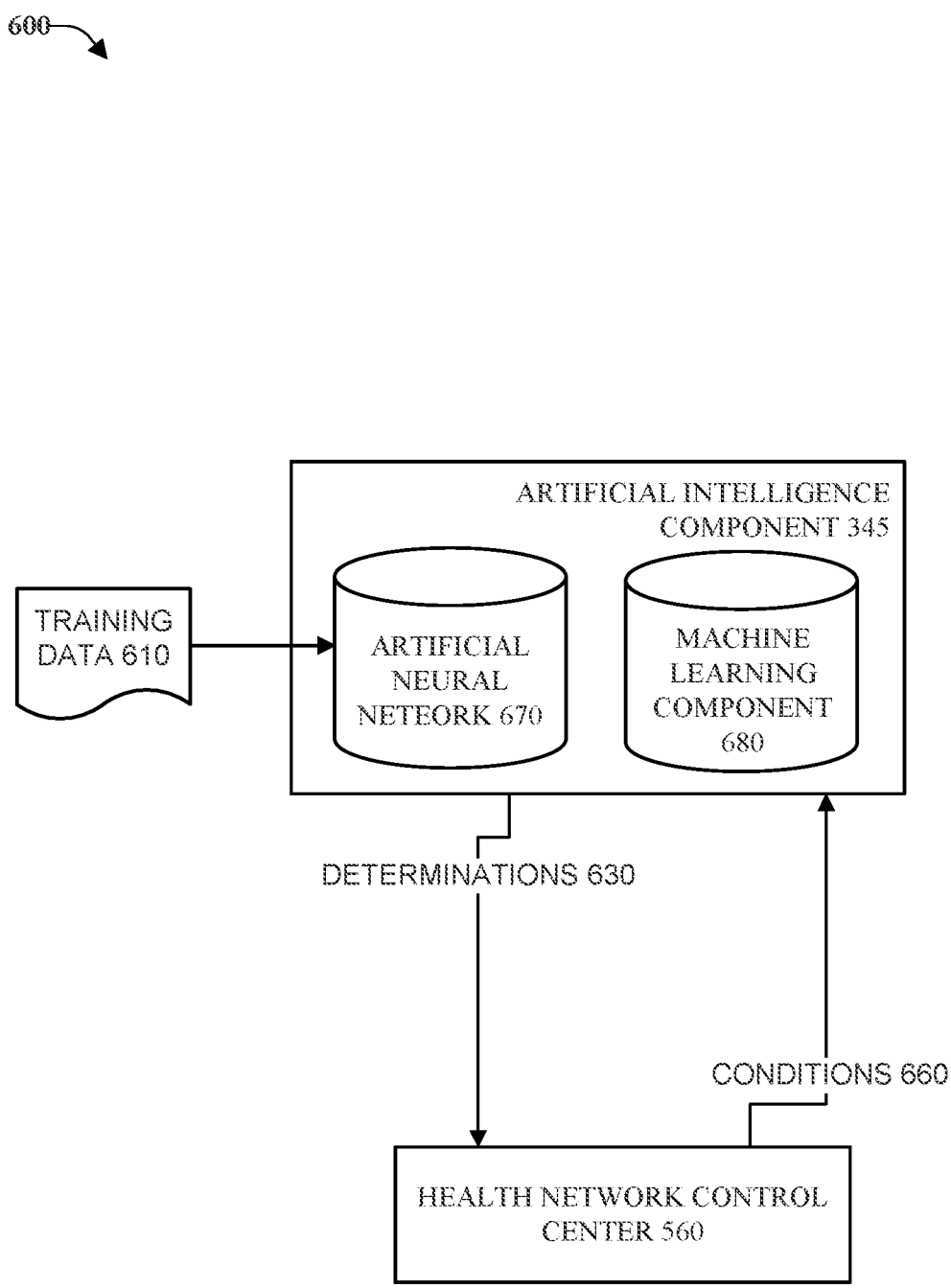
FIG. 6 illustrates an implementation of an example, non-limiting system that can facilitate evaluation of treatment options by utilizing different artificial intelligence approaches, in accordance with one or more embodiments.

FIG. 6 illustrates an implementation of an example, non-limiting system 600 that can facilitate evaluation of treatment options by utilizing different artificial intelligence approaches, in accordance with one or more embodiments. For purposes of brevity, description of like elements and/or processes employed in other embodiments is omitted.

System 600 can include artificial intelligence component 345 that can, in different embodiments, use artificial intelligence and machine learning approaches to assist with determinations discussed above, e.g., selection of a treatment facility 210A-B and allocation of priority to relevant network links. In some implementations, artificial intelligence component 345 can comprise artificial neural network 670 with training data 610 and in additional or alternative embodiments, artificial intelligence component 345 can comprise machine learning component 680.

Other example applications for artificial intelligence as a part of one or more embodiments include treatment resource management and scheduling, identifying preferable routes for ambulance and other medical transports, matching patient symptoms with historical data to identify best practices, as well as selection of a treatment facility.

In certain embodiments, different functions of embodiments discussed above can be facilitated based on classifications, correlations, inferences and/or expressions associated with principles of artificial intelligence. For example, artificial intelligence component 345 can employ expert systems, fuzzy logic, SVMs, Hidden Markov Models (HMMs), greedy search algorithms, rule-based systems, Bayesian models (e.g., Bayesian networks), ANNs, other non-linear training techniques, data fusion, utility-based analytical systems, systems employing Bayesian models, and ensemble machine learning algorithms/methods, including deep neural networks (DNN), reinforcement learning (RL), Bayesian Statistics, long short-term memory (LSTM) networks.

In another example, in one or more embodiments, machine learning models can be incorporated for use by distributed learning agents to analyze one or more of all of the inputs discussed above, e.g., resources of treatment facilities 210A-B, distances between geographic locations 310A-C, network resources allocated and other data sources discussed or suggested from discussions above.

In another aspect, artificial intelligence component 345 that can perform a set of machine learning computations associated with the selection of different slice characteristics. One having skill in the relevant art(s), given the description herein will appreciate that, for example, artificial intelligence component 345 that can operate to perform analysis that can include, but is not limited to: RL analysis, a set of clustering machine learning computations, a set of logistic regression machine learning computations, a set of decision tree machine learning computations, a set of random forest machine learning computations, a set of regression tree machine learning computations, a set of least square machine learning computations, a set of instance-based machine learning computations, a set of regression machine learning computations, a set of support vector regression machine learning computations, a set of k-means machine learning computations, a set of spectral clustering machine learning computations, a set of rule learning machine learning computations, a set of Bayesian machine learning computations, a set of deep Boltzmann machine computations, a set of deep belief network computations, and a set of different machine learning computations to analyze network data, and detect anomalous activities in allocated network slices.

In an example machine learning approach that can be utilized by one or more embodiments, artificial neural network 670 can be optimized (also termed "trained" herein) by submitting optimizing data to the network, e.g., training data 610 that can include results of past determinations, given different situations. It should be noted that this description of employing an artificial neural network 670 is non-limiting, e.g., one or more embodiments can use other types of machine learning algorithms that receive input and perform analysis as described above.

Figure 7:
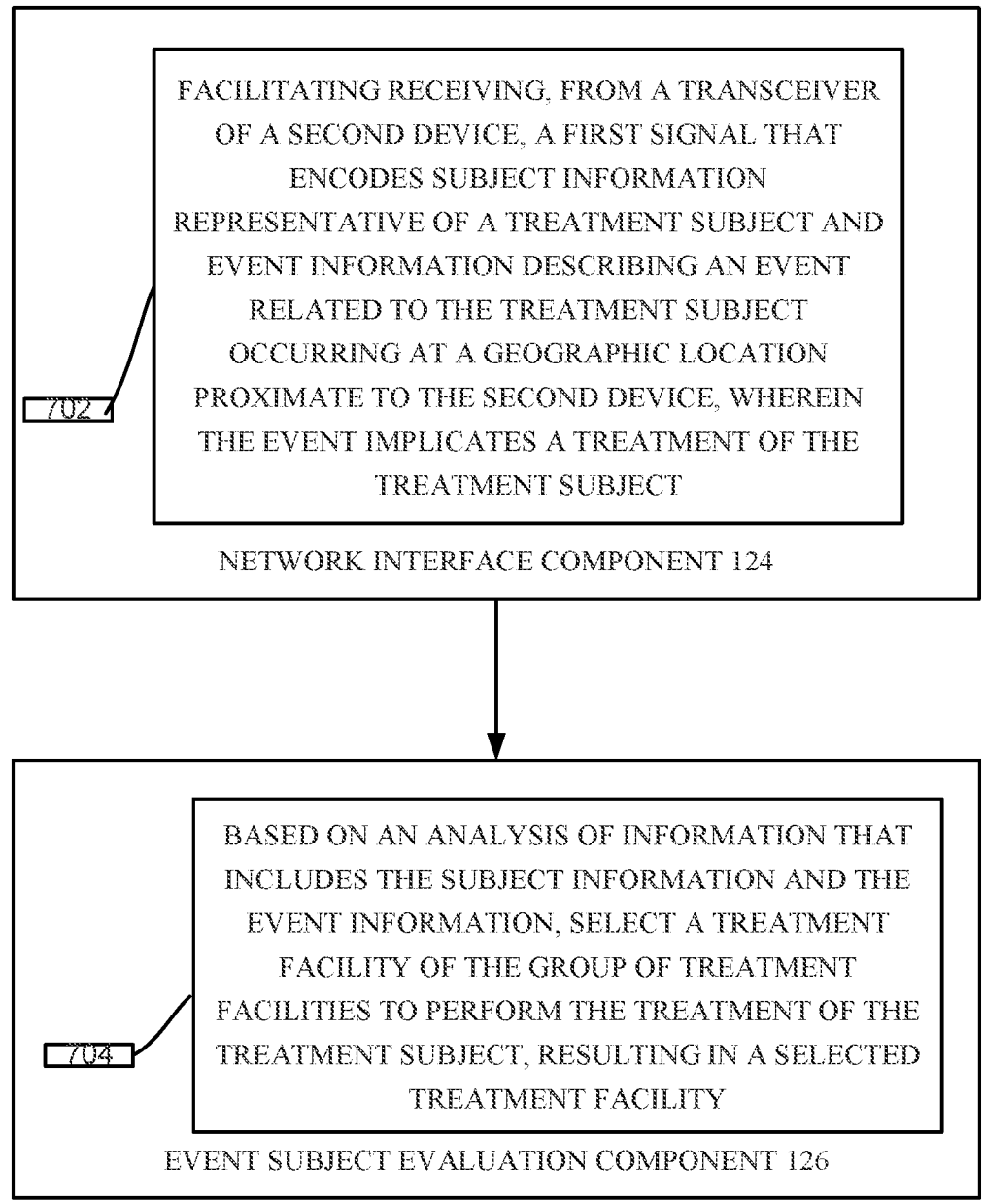
FIG. 7 illustrates an example system that can facilitate operation of a health network control system of information sharing, in accordance with one or more embodiments.

FIG. 7 illustrates an example system 700 that can facilitate operation of a health network control system of information sharing, in accordance with one or more embodiments. For purposes of brevity, description of like elements and/or processes employed in other embodiments is omitted.

In one or more embodiments, network interface component 124, which can in some implementations be configured 702 to facilitate receiving, from a transceiver of a second device, a first wireless signal that is modulated to encode subject information representative of a treatment subject and event information describing an event related to the treatment subject occurring at a geographic location proximate to the second device, wherein the event implicates a treatment of the treatment subject. For example, in one or more embodiments, network interface component 124 can facilitate receiving, from a transceiver 142 of a second device 237, a first wireless signal 217 that is modulated to encode subject information representative of a treatment subject (e.g., patient 232) and event information describing an event 270 related to the treatment subject occurring at a geographic location 230A proximate to the second device 237, wherein the event 270 implicates a treatment of the treatment subject, e.g., emergency medical treatment of patient 232.

In one or more embodiments, event subject evaluation component 126, can in some implementations, be configured 704 to, based on an analysis of information that includes the subject information and the event information, select a treatment facility of the group of treatment facilities to perform the treatment of the treatment subject, resulting in a selected treatment facility. For example, in one or more embodiments, event subject evaluation component 126 can, based on further analysis of information that includes the subject information and the event 270 information, select a treatment facility 210A of the group of treatment facilities to perform the treatment of the treatment subject, resulting in a selected treatment facility.

Figure 8:
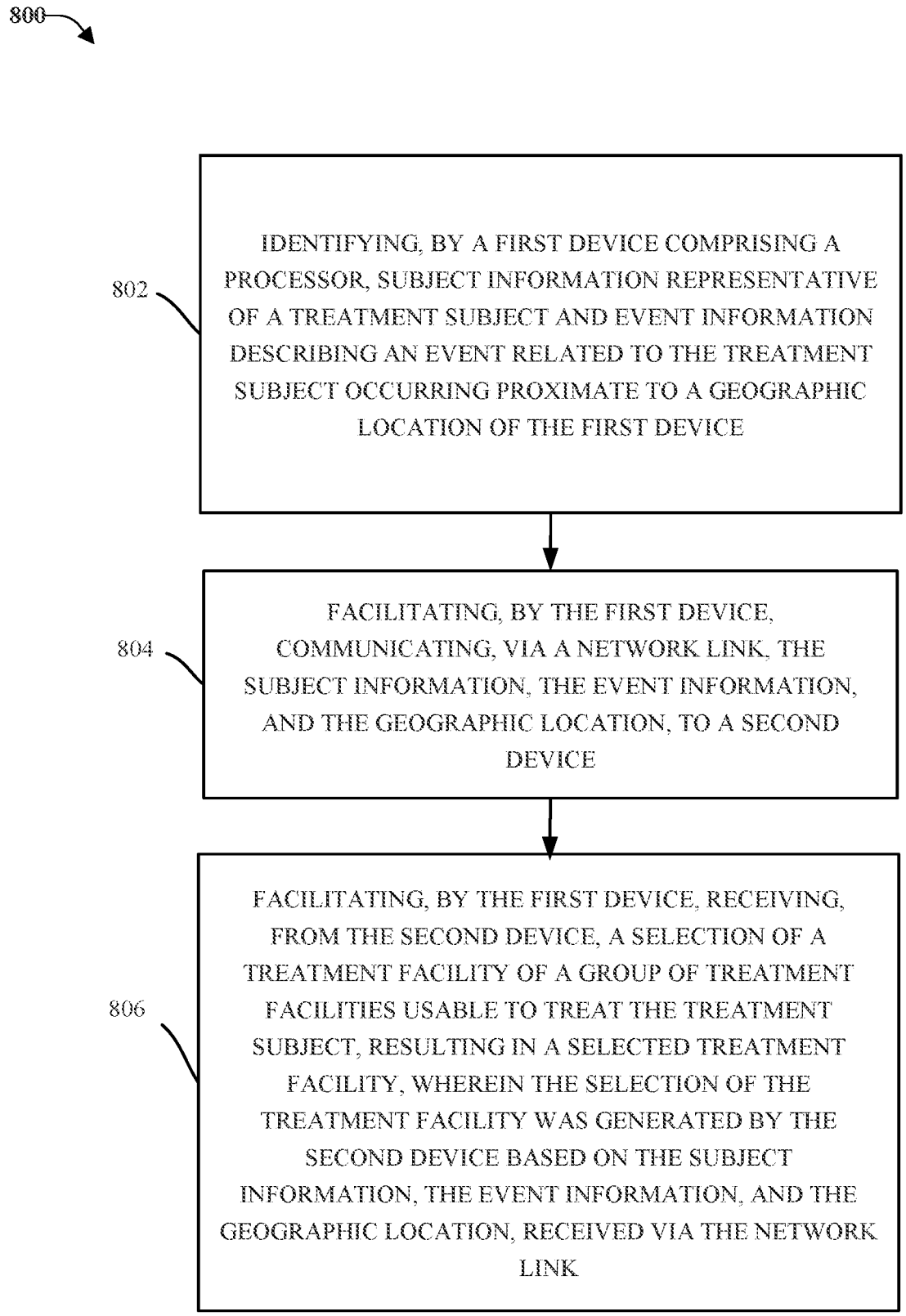
FIG. 8 illustrates a flow diagram of an example method that can facilitate the operation of a health network control system of information sharing, in accordance with one or more embodiments.

FIG. 8 illustrates a flow diagram of an example method 800 that can facilitate the operation of a health network control system of information sharing, in accordance with one or more embodiments. For purposes of brevity, description of like elements and/or processes employed in other embodiments is omitted. At 802, method 800 can comprise identifying, by a first device comprising a processor, subject information representative of a treatment subject and event information describing an event related to the treatment subject occurring proximate to a geographic location of the first device. For example, in one or more embodiments, method 800 can comprise identifying, by a first device comprising a processor, subject information representative of a treatment subject and event information describing an event related to the treatment subject occurring proximate to a geographic location of the first device.

At 804, method 800 can comprise facilitating, by the first device, communicating, via a wireless network link, the subject information, the event information, and the geographic location, to a second device. For example, in one or more embodiments, method 800 can comprise facilitating, by the first device, communicating, via a wireless network link, the subject information, the event information, and the geographic location, to a second device.

At 806, method 800 can comprise facilitating, by the first device, receiving a selection from the second device, of a treatment facility of a group of treatment facilities usable to treat the treatment subject, resulting in a selected treatment facility, wherein the selection of the treatment facility was generated by the second device based on the subject information, the event information, and the geographic location, received via the wireless network link. For example, in one or more embodiments, method 800 can comprise facilitating, by the first device, receiving a selection from the second device, of a treatment facility of a group of treatment facilities usable to treat the treatment subject, resulting in a selected treatment facility, wherein the selection of the treatment facility was generated by the second device based on the subject information, the event information, and the geographic location, received via the wireless network link.

It is to be appreciated that one or more embodiments described herein can utilize various combinations of electrical components, mechanical components, mass storage, circuitry, and extensive, repetitive, rapidly performed, and complicated analysis of data that cannot be replicated in the mind of a human or performed by any number of humans working together. One or more embodiments can provide a technical solution to a technical problem by processing and analyzing utilization data of network slices with functions beyond the capability of a human mind, e.g., the operations of network components including, but not limited to, network interface component 124, facility selecting component 122, and event subject evaluation component 126

According to several embodiments, system 100 can also be fully operational towards performing one or more other functions (e.g., fully powered on, fully executed, etc.) while also performing the various operations of a health network control system of information sharing that are described and suggested herein. It should be appreciated that such simultaneous multi-operational execution is beyond the capability of a human mind. It should also be appreciated that health network control system 100 can obtain, analyze, and process information that is impossible to obtain, analyze, and process manually by an entity, such as a human user. For example, the type, amount, and/or variety of information included in health network control system 100 disclosed herein, can be more complex than information able to be obtained manually by a human user.

Figure 9:
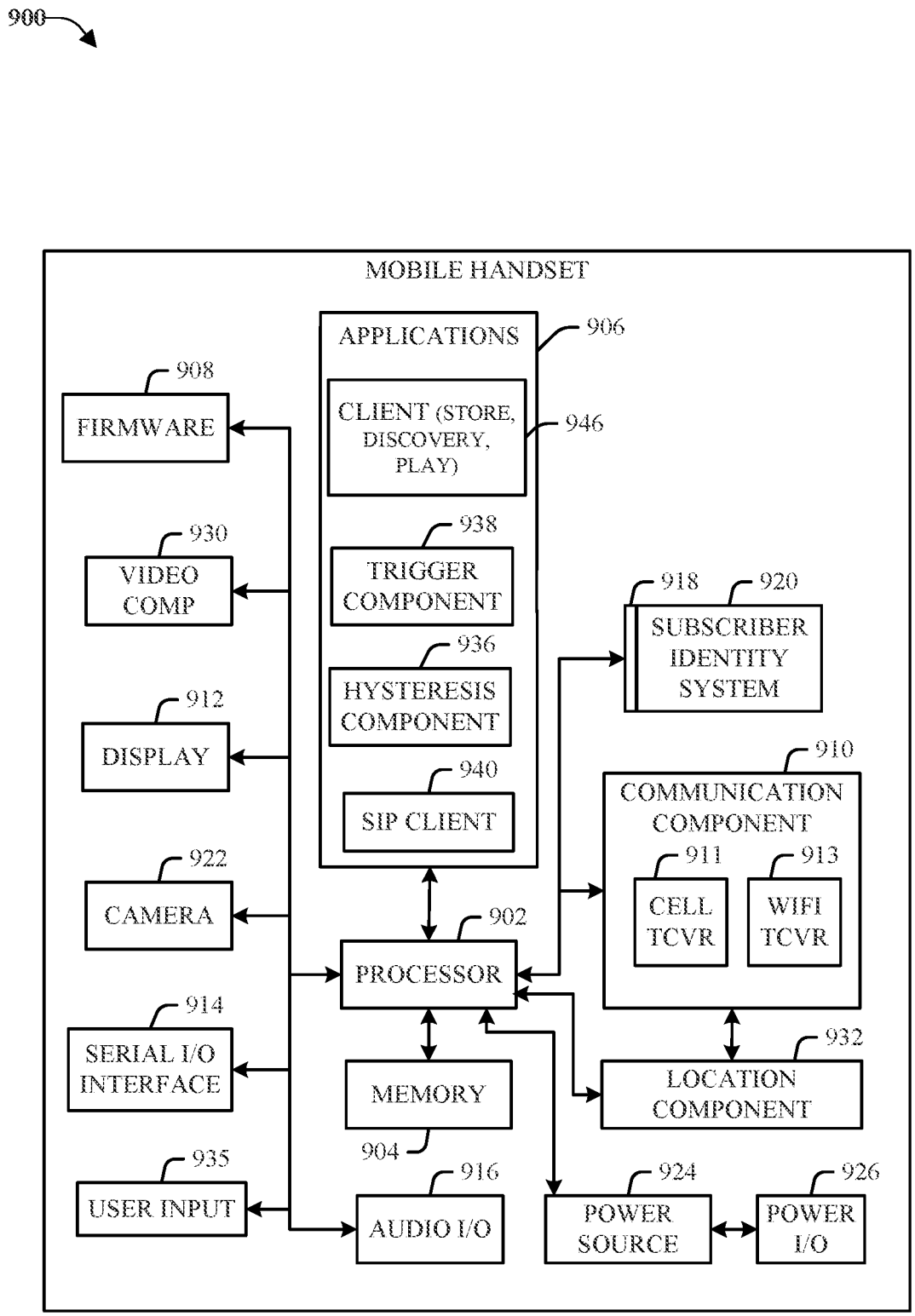
FIG. 9 illustrates an example block diagram of an example mobile handset operable to engage in a system architecture that can facilitate processes described herein, in accordance with one or more embodiments.

FIG. 9 illustrates an example block diagram of an example mobile handset 900 operable to engage in a system architecture that facilitates wireless communications according to one or more embodiments described herein. Although a mobile handset is illustrated herein, it will be understood that other devices can be a mobile device, and that the mobile handset is merely illustrated to provide context for the embodiments of the various embodiments described herein. The following discussion is intended to provide a brief, general description of an example of a suitable environment in which the various embodiments can be implemented. While the description includes a general context of computer-executable instructions embodied on a machine-readable storage medium, those skilled in the art will recognize that the embodiments also can be implemented in combination with other program modules and/or as a combination of hardware and software.

Generally, applications (e.g., program modules) can include routines, programs, components, data structures, etc., that perform particular tasks or implement particular abstract data types. Moreover, those skilled in the art will appreciate that the methods described herein can be practiced with other system configurations, including single-processor or multiprocessor systems, minicomputers, mainframe computers, as well as personal computers, hand-held computing devices, microprocessor-based or programmable consumer electronics, cloud computing environments and the like, each of which can be operatively coupled to one or more associated devices.

As used with discussions of some embodiments herein, a cloud computing environment, the cloud, or other similar terms can refer to computing that can share processing resources and data to one or more computer and other device on an as needed basis to facilitate access to a shared pool of configurable computing resources that can be provisioned and released readily. For example, the preferential allocation of network resources to responder device 140 and network device 150 described above can be facilitated by flexible allocation of cloud computing resources, in accordance with one or more embodiments described herein.

A computing device can typically include a variety of machine-readable media. Machine-readable media can be any available media that can be accessed by the computer and includes both volatile and non-volatile media, removable and non-removable media. By way of example and not limitation, computer-readable media can comprise computer storage media and communication media. Computer storage media can include volatile and/or non-volatile media, removable and/or non-removable media implemented in any method or technology for storage of information, such as computer-readable instructions, data structures, program modules, or other data. Computer storage media can include, but is not limited to, RAM, ROM, EEPROM, flash memory or other memory technology, solid state drive (SSD) or other solid-state storage technology, Compact Disk Read Only Memory (CD ROM), digital video disk (DVD), Blu-ray disk, or other optical disk storage, magnetic cassettes, magnetic tape, magnetic disk storage or other magnetic storage devices, or any other medium which can be used to store the desired information and which can be accessed by the computer. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Communication media typically embodies computer-readable instructions, data structures, program modules, or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media The handset includes a processor 902 for controlling and processing all onboard operations and functions. A memory 904 interfaces to the processor 902 for storage of data and one or more applications 906 (e.g., a video player software, user feedback component software, etc.). Other applications can include voice recognition of predetermined voice commands that facilitate initiation of the user feedback signals. The applications 906 can be stored in the memory 904 and/or in a firmware 908, and executed by the processor 902 from either or both the memory 904 or/and the firmware 908. The firmware 908 can also store startup code for execution in initializing the handset 900. A communications component 910 interfaces to the processor 902 to facilitate wired/wireless communication with external systems, e.g., cellular networks, VoIP networks, and so on. Here, the communications component 910 can also include a suitable cellular transceiver 911 (e.g., a GSM transceiver) and/or an unlicensed transceiver 913 (e.g., Wi-Fi, WiMax) for corresponding signal communications. The handset 900 can be a device such as a cellular telephone, a PDA with mobile communications capabilities, and messaging-centric devices. The communications component 910 also facilitates communications reception from terrestrial radio networks (e.g., broadcast), digital satellite radio networks, and Internet-based radio services networks The handset 900 includes a display 912 for displaying text, images, video, telephony functions (e.g., a Caller ID function), setup functions, and for user input. For example, the display 912 can also be referred to as a "screen" that can accommodate the presentation of multimedia content (e.g., music metadata, messages, wallpaper, graphics, etc.). The display 912 can also display videos and can facilitate the generation, editing and sharing of video quotes. A serial I/O interface 914 is provided in communication with the processor 902 to facilitate wired and/or wireless serial communications (e.g., USB, and/or IEEE 1294) through a hardwire connection, and other serial input devices (e.g., a keyboard, keypad, and mouse). This supports updating and troubleshooting the handset 900, for example. Audio capabilities are provided with an audio I/O component 916, which can include a speaker for the output of audio signals related to, for example, indication that the user pressed the proper key or key combination to initiate the user feedback signal. The audio I/O component 916 also facilitates the input of audio signals through a microphone to record data and/or telephony voice data, and for inputting voice signals for telephone conversations.

The handset 900 can include a slot interface 918 for accommodating a SIC (Subscriber Identity Component) in the form factor of a card Subscriber Identity Module (SIM) or universal SIM 920, and interfacing the SIM card 920 with the processor 902. However, it is to be appreciated that the SIM card 920 can be manufactured into the handset 900, and updated by downloading data and software.

The handset 900 can process IP data traffic through the communications component 910 to accommodate IP traffic from an IP network such as, for example, the Internet, a corporate intranet, a home network, a person area network, etc., through an ISP or broadband cable provider. Thus, VoIP traffic can be utilized by the handset 900 and IP-based multimedia content can be received in either an encoded or a decoded format.

A video processing component 922 (e.g., a camera) can be provided for decoding encoded multimedia content. The video processing component 922 can aid in facilitating the generation, editing, and sharing of video quotes. The handset 900 also includes a power source 924 in the form of batteries and/or an AC power subsystem, which power source 924 can interface to an external power system or charging equipment (not shown) by a power I/O component 926.

The handset 900 can also include a video component 930 for processing video content received and, for recording and transmitting video content. For example, the video component 930 can facilitate the generation, editing and sharing of video quotes. A location tracking component 932 facilitates geographically locating the handset 900. As described hereinabove, this can occur when the user initiates the feedback signal automatically or manually. A user input component 934 facilitates the user initiating the quality feedback signal. The user input component 934 can also facilitate the generation, editing and sharing of video quotes. The user input component 934 can include such conventional input device technologies such as a keypad, keyboard, mouse, stylus pen, and/or touch screen, for example.

Referring again to the applications 906, a hysteresis component 936 facilitates the analysis and processing of hysteresis data, which is utilized to determine when to associate with the access point. A software trigger component 938 can be provided that facilitates triggering of the hysteresis component 936 when the Wi-Fi transceiver 913 detects the beacon of the access point. A SIP client 940 enables the handset 900 to support SIP protocols and register the subscriber with the SIP registrar server. The applications 906 can also include a client 942 that provides at least the capability of discovery, play and store of multimedia content, for example, music.

The handset 900, as indicated above related to the communications component 910, includes an indoor network radio transceiver 913 (e.g., Wi-Fi transceiver). This function supports the indoor radio link, such as IEEE 802.11, for the dual-mode GSM handset 900. The handset 900 can accommodate at least satellite radio services through a handset that can combine wireless voice and digital radio chipsets into a single handheld device.

As discussed with FIG. 1, network 190 can include a wireless communication system, and thus can include one or more communication service provider networks that facilitate providing wireless communication services to various user equipments included in the one or more communication service provider networks. The one or more communication service provider networks can include various types of disparate networks, including but not limited to: cellular networks, femto networks, picocell networks, microcell networks, internet protocol (IP) networks Wi-Fi service networks, broadband service network, enterprise networks, cloud based networks, and the like. For example, in at least one implementation, system 100 can be or include a large scale wireless communication network that spans various geographic areas. According to this implementation, the one or more communication service provider networks can be or include the wireless communication network and/or various additional devices and components of the wireless communication network (e.g., additional network devices and cell, additional user equipments, network server devices, etc.).

The network device 150 can be connected to one or more communication service provider networks via one or more backhaul links or the like (not shown). For example, the one or more backhaul links can comprise wired link components, such as a T1/E1 phone line, a digital subscriber line (DSL) (e.g., either synchronous or asynchronous), an asymmetric DSL (ADSL), an optical fiber backbone, a coaxial cable, and the like.

Network 190 can employ various cellular systems, technologies, and modulation schemes to facilitate wireless radio communications between devices. While example embodiments include use of 5G new radio (NR) systems, one or more embodiments discussed herein can be applicable to any radio access technology (RAT) or multi-RAT system, including where user equipments operate using multiple carriers, e.g. LTE FDD/TDD, GSM/GERAN, CDMA2000, etc. For example, wireless communication system 200 can operate in accordance with global system for mobile communications (GSM), universal mobile telecommunications service (UMTS), long term evolution (LTE), LTE frequency division duplexing (LTE FDD, LTE time division duplexing (TDD), high speed packet access (HSPA), code division multiple access (CDMA), wideband CDMA (WCMDA), CDMA2000, time division multiple access (TDMA), frequency division multiple access (FDMA), multi-carrier code division multiple access (MC-CDMA), single-carrier code division multiple access (SC-CDMA), single-carrier FDMA (SC-FDMA), orthogonal frequency division multiplexing (OFDM), discrete Fourier transform spread OFDM (DFT-spread OFDM) single carrier FDMA (SC-FDMA), Filter bank based multi-carrier (FBMC), zero tail DFT-spread-OFDM (ZT DFT-s-OFDM), generalized frequency division multiplexing (GFDM), fixed mobile convergence (FMC), universal fixed mobile convergence (UFMC), unique word OFDM (UW-OFDM), unique word DFT-spread OFDM (UW DFT-Spread-OFDM), cyclic prefix OFDM CP-OFDM, resource-block-filtered OFDM, Wi Fi, WLAN, WiMax, and the like. However, various features and functionalities of system 100 are particularly described wherein the devices (e.g., event responder device 140 and network device 150) of system 100 are configured to communicate wireless signals using one or more multi carrier modulation schemes, wherein data symbols can be transmitted simultaneously over multiple frequency subcarriers (e.g., OFDM, CP-OFDM, DFT-spread OFMD, UFMC, FMBC, etc.). The embodiments are applicable to single carrier as well as to multicarrier (MC) or carrier aggregation (CA) operation of the user equipment. The term carrier aggregation (CA) is also called (e.g. interchangeably called) "multi-carrier system", "multi-cell operation", "multi-carrier operation", "multi-carrier" transmission and/or reception. Note that some embodiments are also applicable for Multi RAB (radio bearers) on some carriers (that is data plus speech is simultaneously scheduled).

Various embodiments described herein can be configured to provide and employ 5G wireless networking features and functionalities. With 5G networks that may use waveforms that split the bandwidth into several sub bands, different types of services can be accommodated in different sub bands with the most suitable waveform and numerology, leading to improved spectrum utilization for 5G networks. Notwithstanding, in the mmWave spectrum, the millimeter waves have shorter wavelengths relative to other communications waves, whereby mmWave signals can experience severe path loss, penetration loss, and fading. However, the shorter wavelength at mmWave frequencies also allows more antennas to be packed in the same physical dimension, which allows for large-scale spatial multiplexing and highly directional beamforming.

Figure 10:
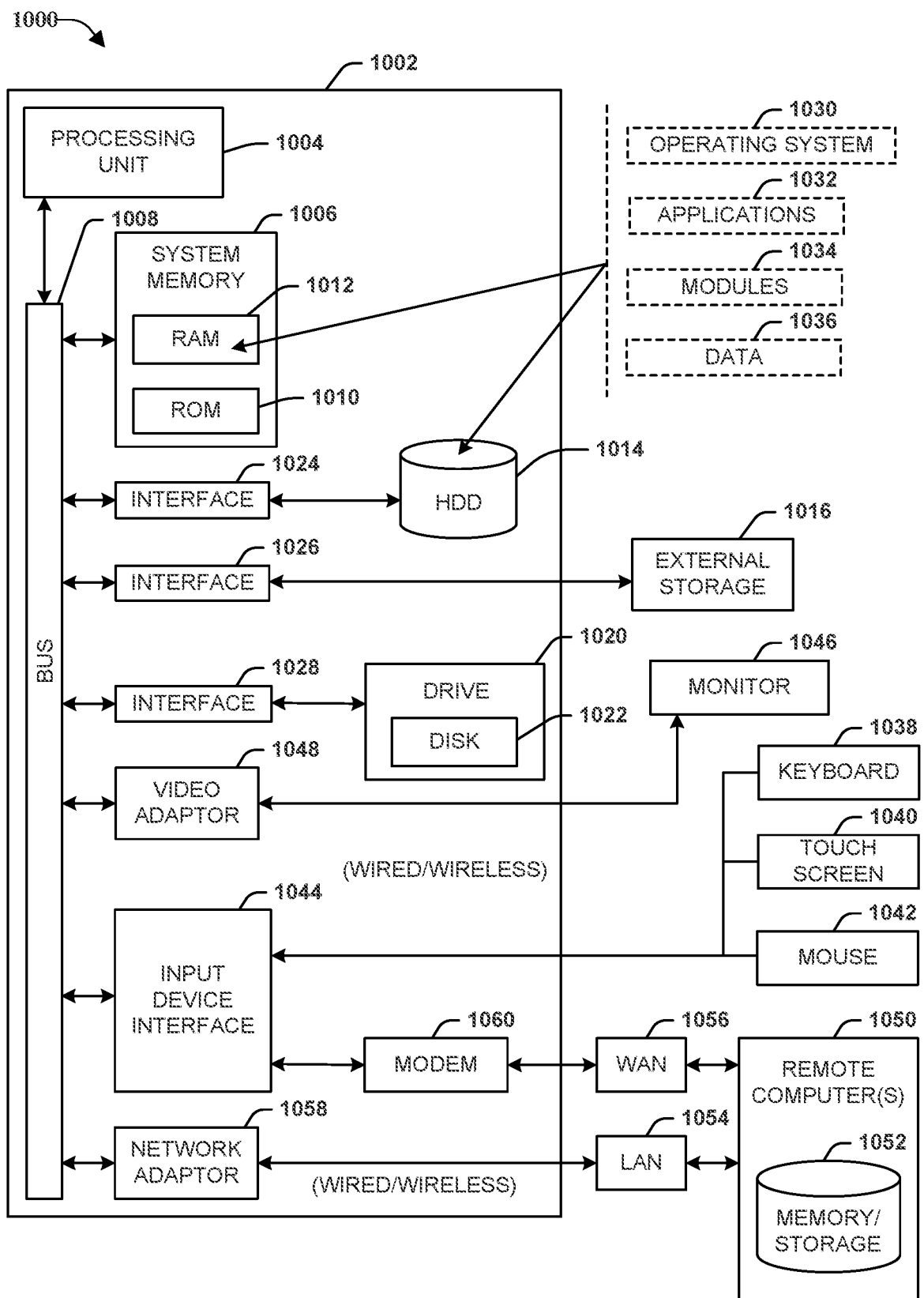
FIG. 10 illustrates an example block diagram of an example computer operable to engage in a system architecture that can facilitate processes described herein, in accordance with one or more embodiments.

FIG. 10 provides additional context for various embodiments described herein, intended to provide a brief, general description of a suitable operating environment 1000 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 10, the example operating environment 1000 for implementing various embodiments of the aspects described herein includes a computer 1002, the computer 1002 including a processing unit 1004, a system memory 1006 and a system bus 1008. The system bus 1008 couples system components including, but not limited to, the system memory 1006 to the processing unit 1004. The processing unit 1004 can be any of various commercially available processors. Dual microprocessors and other multi-processor architectures can also be employed as the processing unit 1004.

The system bus 1008 can be any of several types of bus structure that can further interconnect to a memory bus (with or without a memory controller), a peripheral bus, and a local bus using any of a variety of commercially available bus architectures. The system memory 1006 includes ROM 1010 and RAM 1012. A basic input/output system (BIOS) can be stored in a non-volatile memory such as ROM, erasable programmable read only memory (EPROM), EEPROM, which BIOS contains the basic routines that help to transfer information between elements within the computer 1002, such as during startup. The RAM 1012 can also include a high-speed RAM such as static RAM for caching data.

The computer 1002 further includes an internal hard disk drive (HDD) 1014 (e.g., EIDE, SATA), one or more external storage devices 1016 (e.g., a magnetic floppy disk drive (FDD) 1016, a memory stick or flash drive reader, a memory card reader, etc.) and a drive 1020, e.g., such as a solid state drive, an optical disk drive, which can read or write from a disk 1022, such as a CD-ROM disc, a DVD, a BD, etc. Alternatively, where a solid state drive is involved, disk 1022 would not be included, unless separate. While the internal HDD 1014 is illustrated as located within the computer 1002, the internal HDD 1014 can also be configured for external use in a suitable chassis (not shown). Additionally, while not shown in environment 1000, a solid state drive (SSD) could be used in addition to, or in place of, an HDD 1014. The HDD 1014, external storage device(s) 1016 and drive 1020 can be connected to the system bus 1008 by an HDD interface 1024, an external storage interface 1026 and a drive interface 1028, respectively. The interface 1024 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 1002, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1012, including an operating system 1030, one or more application programs 1032, other program modules 1034 and program data 1036. All or portions of the operating system, applications, modules, and/or data can also be cached in the RAM 1012. The systems and methods described herein can be implemented utilizing various commercially available operating systems or combinations of operating systems.

Computer 1002 can optionally comprise emulation technologies. For example, a hypervisor (not shown) or other intermediary can emulate a hardware environment for operating system 1030, and the emulated hardware can optionally be different from the hardware illustrated in FIG. 10. In such an embodiment, operating system 1030 can comprise one virtual machine (VM) of multiple VMs hosted at computer 1002. Furthermore, operating system 1030 can provide runtime environments, such as the Java runtime environment or the .NET framework, for applications 1032. Runtime environments are consistent execution environments that allow applications 1032 to run on any operating system that includes the runtime environment. Similarly, operating system 1030 can support containers, and applications 1032 can be in the form of containers, which are lightweight, standalone, executable packages of software that include, e.g., code, runtime, system tools, system libraries and settings for an application.

Further, computer 1002 can be enable with a security module, such as a trusted processing module (TPM). For instance, with a TPM, boot components hash next in time boot components, and wait for a match of results to secured values, before loading a next boot component. This process can take place at any layer in the code execution stack of computer 1002, e.g., applied at the application execution level or at the operating system (OS) kernel level, thereby enabling security at any level of code execution.

A user can enter commands and information into the computer 1002 through one or more wired/wireless input devices, e.g., a keyboard 1038, a touch screen 1040, and a pointing device, such as a mouse 1042. Other input devices (not shown) can include a microphone, an infrared (IR) remote control, a radio frequency (RF) remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1004 through an input device interface 1044 that can be coupled to the system bus 1008, but can be connected by other interfaces, such as a parallel port, an IEEE 1394 serial port, a game port, a USB port, an IR interface, a BLUETOOTH® interface, etc.

A monitor 1046 or other type of display device can be also connected to the system bus 1008 via an interface, such as a video adapter 1048. In addition to the monitor 1046, a computer typically includes other peripheral output devices (not shown), such as speakers, printers, etc.

The computer 1002 can operate in a networked environment using logical connections via wired and/or wireless communications to one or more remote computers, such as a remote computer(s) 1050. The remote computer(s) 1050 can be a workstation, a server computer, a router, a personal computer, portable computer, microprocessor-based entertainment appliance, a peer device or other common network node, and typically includes many or all of the elements described relative to the computer 1002, although, for purposes of brevity, only a memory/storage device 1052 is illustrated. The logical connections depicted include wired/wireless connectivity to a local area network (LAN) 1054 and/or larger networks, e.g., a wide area network (WAN) 1056. Such LAN and WAN networking environments are commonplace in offices and companies, and facilitate enterprise-wide computer networks, such as intranets, all of which can connect to a global communications network, e.g., the Internet.

When used in a LAN networking environment, the computer 1002 can be connected to the local network 1054 through a wired and/or wireless communication network interface or adapter 1058. The adapter 1058 can facilitate wired or wireless communication to the LAN 1054, which can also include a wireless access point (AP) disposed thereon for communicating with the adapter 1058 in a wireless mode.

When used in a WAN networking environment, the computer 1002 can include a modem 1060 or can be connected to a communications server on the WAN 1056 via other means for establishing communications over the WAN 1056, such as by way of the Internet. The modem 1060, which can be internal or external and a wired or wireless device, can be connected to the system bus 1008 via the input device interface 1044. In a networked environment, program modules depicted relative to the computer 1002 or portions thereof, can be stored in the remote memory/storage device 1052. It will be appreciated that the network connections shown are example and other means of establishing a communications link between the computers can be used.

When used in either a LAN or WAN networking environment, the computer 1002 can access cloud storage systems or other network-based storage systems in addition to, or in place of, external storage devices 1016 as described above, such as but not limited to a network virtual machine providing one or more aspects of storage or processing of information. Generally, a connection between the computer 1002 and a cloud storage system can be established over a LAN 1054 or WAN 1056 e.g., by the adapter 1058 or modem 1060, respectively. Upon connecting the computer 1002 to an associated cloud storage system, the external storage interface 1026 can, with the aid of the adapter 1058 and/or modem 1060, manage storage provided by the cloud storage system as it would other types of external storage. For instance, the external storage interface 1026 can be configured to provide access to cloud storage sources as if those sources were physically connected to the computer 1002.

The computer 1002 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

The above description of illustrated embodiments of the subject disclosure, including what is described in the Abstract, is not intended to be exhaustive or to limit the disclosed embodiments to the precise forms disclosed. While specific embodiments and examples are described herein for illustrative purposes, various modifications are possible that are considered within the scope of such embodiments and examples, as those skilled in the relevant art can recognize.

In this regard, while the disclosed subject matter has been described in connection with various embodiments and corresponding Figures, where applicable, it is to be understood that other similar embodiments can be used or modifications and additions can be made to the described embodiments for performing the same, similar, alternative, or substitute function of the disclosed subject matter without deviating therefrom. Therefore, the disclosed subject matter should not be limited to any single embodiment described herein, but rather should be construed in breadth and scope in accordance with the appended claims below.

Further to the description above, as it employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Processors can exploit nano-scale architectures such as, but not limited to, molecular and quantum-dot based transistors, switches and gates, in order to optimize space usage or enhance performance of user equipment. A processor may also be implemented as a combination of computing processing units.

In the subject specification, terms such as "store," "storage," "data store," "data storage," "database," and substantially any other information storage component relevant to operation and functionality of a component, refer to "memory components," or entities embodied in a "memory" or components comprising the memory. It will be appreciated that the memory components described herein can be either volatile memory or nonvolatile memory, or can include both volatile and nonvolatile memory.

As used in this application, the terms "component," "system," "platform," "layer," "selector," "interface," and the like are intended to refer to a computer-related entity or an entity related to an operational apparatus with one or more specific functionalities, wherein the entity can be either hardware, a combination of hardware and software, software, or software in execution. As an example, a component may be, but is not limited to being, a process running on a processor, a processor, an object, an executable, a thread of execution, a program, and/or a computer. By way of illustration and not limitation, both an application running on a server and the server can be a component. One or more components may reside within a process and/or thread of execution and a component may be localized on one computer and/or distributed between two or more computers. In addition, these components can execute from various computer readable media, device readable storage devices, or machine readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor, wherein the processor can be internal or external to the apparatus and executes at least a part of the software or firmware application. As yet another example, a component can be an apparatus that provides specific functionality through electronic components without mechanical parts, the electronic components can include a processor therein to execute software or firmware that confers at least in part the functionality of the electronic components.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

Moreover, terms like "user equipment (UE)," "mobile station," "mobile," "subscriber station," "subscriber equipment," "access terminal," "terminal," "handset," and similar terminology, refer to a wireless device utilized by a subscriber or user of a wireless communication service to receive or convey data, control, voice, video, sound, gaming, or substantially any data-stream or signaling-stream. The foregoing terms are utilized interchangeably in the subject specification and related drawings. Likewise, the terms "access point (AP)," "base station," "NodeB," "evolved Node B (eNodeB)," "home Node B (HNB)," "home access point (HAP)," "cell device," "sector," "cell," and the like, are utilized interchangeably in the subject application, and refer to a wireless network component or appliance that serves and receives data, control, voice, video, sound, gaming, or substantially any data-stream or signaling-stream to and from a set of subscriber stations or provider enabled devices. Data and signaling streams can include packetized or frame-based flows.

Additionally, the terms "core-network", "core", "core carrier network", "carrier-side", or similar terms can refer to components of a telecommunications network that typically provides some or all of aggregation, authentication, call control and switching, charging, service invocation, or gateways. Aggregation can refer to the highest level of aggregation in a service provider network wherein the next level in the hierarchy under the core nodes is the distribution networks and then the edge networks. User equipments do not normally connect directly to the core networks of a large service provider but can be routed to the core by way of a switch or radio area network. Authentication can refer to determinations regarding whether the user requesting a service from the telecom network is authorized to do so within this network or not. Call control and switching can refer determinations related to the future course of a call stream across carrier equipment based on the call signal processing. Charging can be related to the collation and processing of charging data generated by various network nodes. Two common types of charging mechanisms found in present day networks can be prepaid charging and postpaid charging. Service invocation can occur based on some explicit action (e.g. call transfer) or implicitly (e.g., call waiting). It is to be noted that service "execution" may or may not be a core network functionality as third party network/nodes may take part in actual service execution. A gateway can be present in the core network to access other networks. Gateway functionality can be dependent on the type of the interface with another network.

Furthermore, the terms "user," "subscriber," "customer," "consumer," "prosumer," "agent," and the like are employed interchangeably throughout the subject specification, unless context warrants particular distinction(s) among the terms. It should be appreciated that such terms can refer to human entities or automated components (e.g., supported through artificial intelligence, as through a capacity to make inferences based on complex mathematical formalisms), that can provide simulated vision, sound recognition and so forth.

Aspects, features, or advantages of the subject matter can be exploited in substantially any, or any, wired, broadcast, wireless telecommunication, radio technology or network, or combinations thereof. Non-limiting examples of such technologies or networks include Geocast technology; broadcast technologies (e.g., sub-Hz, ELF, VLF, LF, MF, HF, VHF, UHF, SHF, THz broadcasts, etc.); Ethernet; X.25; powerline-type networking (e.g., PowerLine AV Ethernet, etc.); femto-cell technology; Wi-Fi; Worldwide Interoperability for Microwave Access (WiMAX); Enhanced General Packet Radio Service (Enhanced GPRS); Third Generation Partnership Project (3GPP or 3G) Long Term Evolution (LTE); 3GPP Universal Mobile Telecommunications System (UMTS) or 3GPP UMTS; Third Generation Partnership Project 2 (3GPP2) Ultra Mobile Broadband (UMB); High Speed Packet Access (HSPA); High Speed Downlink Packet Access (HSDPA); High Speed Uplink Packet Access (HSUPA); GSM Enhanced Data Rates for GSM Evolution (EDGE) Radio Access Network (RAN) or GERAN; UMTS Terrestrial Radio Access Network (UTRAN); or LTE Advanced.

What has been described above includes examples of systems and methods illustrative of the disclosed subject matter. It is, of course, not possible to describe every combination of components or methods herein. One of ordinary skill in the art may recognize that many further combinations and permutations of the disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

While the various embodiments are susceptible to various modifications and alternative constructions, certain illustrated implementations thereof are shown in the drawings and have been described above in detail. It should be understood, however, that there is no intention to limit the various embodiments to the specific forms disclosed, but on the contrary, the intention is to cover all modifications, alternative constructions, and equivalents falling within the spirit and scope of the various embodiments.

In addition to the various implementations described herein, it is to be understood that other similar implementations can be used, or modifications and additions can be made to the described implementation(s) for performing the same or equivalent function of the corresponding implementation(s) without deviating therefrom. Still further, multiple processing chips or multiple devices can share the performance of one or more functions described herein, and similarly, storage can be affected across a plurality of devices. Accordingly, the embodiments are not to be limited to any single implementation, but rather are to be construed in breadth, spirit and scope in accordance with the appended claims.

What is claimed is:

1. First equipment, comprising:
a processor; and
a memory that stores executable instructions that, when executed by the processor, facilitate performance of operations, comprising:
receiving, from a transceiver of second equipment, a first signal via a network link that encodes subject information representative of a status of a treatment subject and event information describing an event related to the treatment subject occurring at a geographic location proximate to the second equipment, wherein the event implicates a treatment of the treatment subject, wherein the subject information comprises a vital sign of the treatment subject measured by a medical monitoring device;
based on the status of the treatment subject, changing a priority assigned to network communications supporting treatment of the treatment subject, wherein changing the priority comprises changing a quality of service specification applicable to the network link;
querying an artificial neural network based on the status of the treatment subject, the event information, the treatment of the treatment subject, and facility information representative of a group of treatment facilities, resulting in a treatment facility of the group of treatment facilities being identified by a response to the query, to perform the treatment of the treatment subject, resulting in a selected treatment facility, wherein the artificial neural network was trained based on historical information associated with the group of treatment facilities; and
communicating, to the transceiver of the second equipment, a second signal encoding selected facility information corresponding to the selected treatment facility.

2. The first equipment of claim 1, wherein the operations further comprise, based on the status of the treatment subject and the priority assigned to the network communications supporting treatment of treatment subject, allocating network resources to communication by the second equipment.

3. The first equipment of claim 2, wherein the medical monitoring device comprises a blood pressure monitoring device.

4. The first equipment of claim 1, wherein the facility information comprises respective treatment resource availabilities of respective ones of the group of the treatment facilities.

5. The first equipment of claim 1, wherein the historical information comprises information related to elements comprising other treatment subjects other than the treatment subject and other events other than the event.

6. The first equipment of claim 5, wherein the historical information comprises information analyzed using an artificial intelligence regression analysis of the other treatment subjects and the other events.

7. The first equipment of claim 6, wherein the operations further comprise, based on the analysis of the subject information and the event information, facilitating, by the first equipment, a provision of treatment by an event responder that responded to the event, the provision of treatment to be initiated before completion of transport to the selected treatment facility.

8. The first equipment of claim 1, wherein the operations further comprise, based on the subject information, retrieving a record corresponding to the treatment subject, and wherein selecting the treatment facility is further based on the record.

9. The first equipment of claim 8, wherein retrieving the record corresponding to the treatment subject comprises retrieving the record from a mobile device of the treatment subject.

10. A method, comprising:
identifying, by a first device comprising a processor, subject information representative of a treatment subject and event information describing an event related to the treatment subject occurring proximate to a geographic location of the first device, wherein the subject information comprises a vital sign of the treatment subject measured by a medical monitoring device;
facilitating, by the first device, communicating, via a network link, the subject information, the event information, and the geographic location, to a second device, wherein, based on the subject information, the second device assigns a priority to network communications supporting treatment of the treatment subject, wherein the priority assigned comprises is based on a quality of service limit applicable to the network link; and
facilitating, by the first device, receiving, from the second device, a selection of a treatment facility of a group of treatment facilities usable to treat the treatment subject, resulting in a selected treatment facility, wherein the selection of the treatment facility was generated by the second device querying an artificial neural network based on the subject information, the event information, the geographic location, and facility information representative of a group of treatment facilities, wherein the artificial neural network was trained based on historical information associated with the group of treatment facilities.

11. The method of claim 10, wherein the facility information comprises treatment resource availabilities of respective ones of the group of the treatment facilities.

12. The method of claim 11, further comprising, facilitating, by the first device, receiving, via the network link from the second device, an alternate selection of an alternate treatment facility of the group of treatment facilities to treat the treatment subject, wherein the second device selected the alternate treatment facility based on the subject information and updated treatment resource availability.

13. The method of claim 10, wherein the selecting of the treatment facility was further based on historical information related to elements comprising other treatment subjects and other events.

14. The method of claim 13, wherein the group of treatment facilities was selected based on the geographic location.

15. The method of claim 10, further comprising, based on an analysis of the subject information and the event information, facilitating, by the first device, a provision of treatment by an event responder that responded to the event, the provision of treatment to be initiated before completion of transport to the selected treatment facility.

16. The method of claim 15, further comprising facilitating, by the first device, establishing communication with the selected treatment facility, wherein the provision of treatment by the event responder comprises the provision of treatment by the event responder based on the communication with the selected treatment facility, and wherein the provision of treatment is initiated before completion of transport to the selected treatment facility.

17. A non-transitory machine-readable medium, comprising executable instructions that, when executed by a processor, facilitate performance of operations, comprising:
receiving facility information representative of a group of treatment facilities;
receiving, from a first responder device, a signal modulated to comprise patient information representative of a patient and event information describing an event related to the patient occurring at a geographic location proximate to the first responder device, wherein the event implicates treatment of the patient at a treatment facility of the group of treatment facilities, wherein the patient information comprises a characteristic of the patient measured by a medical monitoring device;
based on the patient information, assigning a priority to network communications supporting treatment of the patient, wherein the priority is based on a quality of service requirement for the network communications;
querying an artificial neural network based on the patient information, the event information, the geographic location, and facility information representative of the group of treatment facilities, wherein the artificial neural network was trained based on historical information associated with the group of treatment facilities; and
based on a response to the query, selecting a selected treatment facility of the group of treatment facilities to use for the treatment of the patient.

18. The non-transitory machine-readable medium of claim 17, wherein the operations further comprise:
receiving updated event information from the first responder device; and
based on the updated event information, selecting an alternate treatment facility.

19. The non-transitory machine-readable medium of claim 17, wherein the operations further comprise, based on the patient information, obtaining a medical record corresponding to the patient, and wherein selecting the selected treatment facility is further based on the medical record.

20. The non-transitory machine-readable medium of claim 17, wherein selecting the selected treatment facility is further based on the treatment of the patient.

* * * * *